(12) United States Patent
Jennings et al.

(10) Patent No.: US 6,302,577 B1
(45) Date of Patent: Oct. 16, 2001

(54) MICROWAVE APPARATUS AND METHOD FOR ACHIEVING ACCURATE WEIGHT MEASUREMENTS

(75) Inventors: William Edward Jennings, Wingate; Cindy Rushing Moser, Monroe, both of NC (US)

(73) Assignee: CEM Corporation, Matthews, NC (US)

( * ) Notice: Subject to any disclaimer, the term of this patent is extended or adjusted under 35 U.S.C. 154(b) by 0 days.

(21) Appl. No.: 09/397,825

(22) Filed: Sep. 17, 1999

(51) Int. Cl.[7] .................................................. G01N 25/56
(52) U.S. Cl. .............................. 374/14; 374/14; 177/245; 177/145; 73/76
(58) Field of Search .................................. 177/245, 145; 73/76; 374/14

(56) References Cited

U.S. PATENT DOCUMENTS

| | | |
|---|---|---|
| 4,142,403 | 3/1979 | Lohnes et al. . |
| 4,291,775 * | 9/1981 | Collins ................................. 177/245 |
| 4,316,384 * | 2/1982 | Pommer et al. .......................... 73/76 |
| 4,438,500 | 3/1984 | Collins et al. . |
| 4,441,002 | 4/1984 | Teich et al. . |
| 4,457,632 | 7/1984 | Collins et al. . |
| 4,485,284 * | 11/1984 | Pakulis ................................... 374/14 |
| 4,554,132 | 11/1985 | Collins . |
| 4,566,312 | 1/1986 | Collins et al. . |
| 4,651,285 | 3/1987 | Collins et al. . |
| 4,681,996 | 7/1987 | Collins et al. . |
| 4,753,889 | 6/1988 | Collins . |
| 5,349,138 * | 9/1994 | Dong ..................................... 177/245 |
| 5,402,672 * | 4/1995 | Bradford .............................. 177/245 |

FOREIGN PATENT DOCUMENTS

3814959 * 11/1989 (DE) ..................................... 177/145

* cited by examiner

Primary Examiner—Randy W. Gibson
Assistant Examiner—Jason P. Gilchrist
(74) Attorney, Agent, or Firm—Summa & Allan, P.A.

(57) ABSTRACT

The invention is an apparatus and method for obtaining accurate sample weight measurements during sample heating within a heating cavity by substantially reducing the convection currents that disrupt accurate sample weight measurement. The apparatus includes a heating cavity in which a sample can be placed, a source for introducing microwaves into the heating cavity, and an analytical balance for measuring the weight of the sample while the sample is in the cavity, and an air shield that is secured to the inside of the heating cavity so that the air shield will not contact the analytical balance. The air shield, which is made of material that is permeable to microwave radiation and yet absorbent of volatiles, is positioned in the heating cavity to reduce the convection current rising from the sample as the sample is heated.

19 Claims, 3 Drawing Sheets

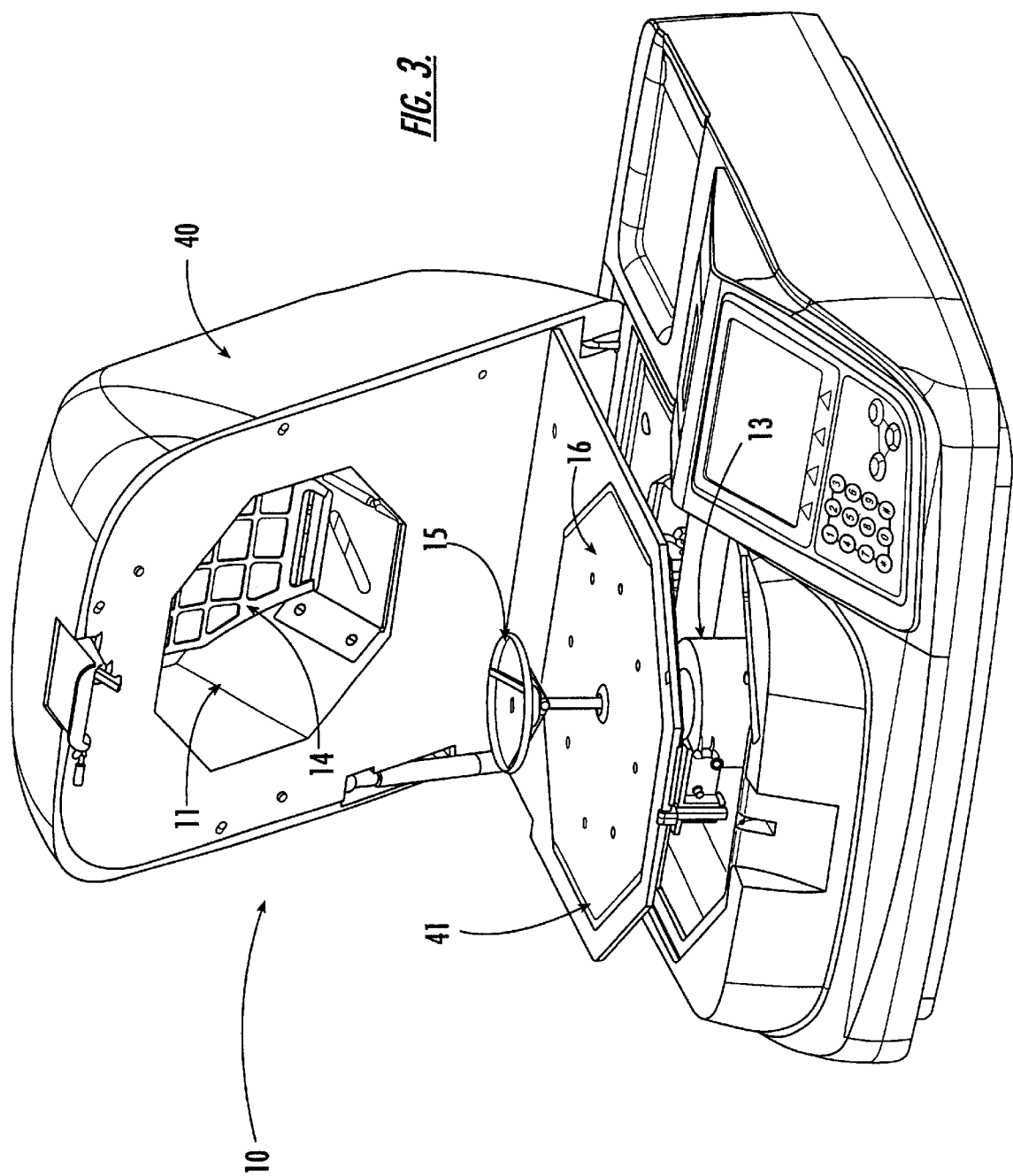

MICROWAVE APPARATUS AND METHOD FOR ACHIEVING ACCURATE WEIGHT MEASUREMENTS

This application is related to and commonly assigned applications Ser. No. 09/398,129 (Microwave volatiles Analyzer with High Efficiency Cavity) and Ser. No. 09/397,825 (Method for Correcting Weight Measurement Errors during Microwave Heating), which are filed concurrently with this application.

FIELD OF THE INVENTION

The invention relates to measuring sample weights during sample heating. In particular, the present invention promotes accurate weight measurements by employing a microwave permeable air shield that substantially reduces disruptive convection currents within a heating cavity. The invention is also a method of using this apparatus to accurately measure the weight of a sample that is undergoing microwave heating.

BACKGROUND OF THE INVENTION

There are analytical procedures for high-speed, quantitative analysis of various substances (e.g., agricultural commodities, foodstuffs, dairy products, paints, coatings, paper products, and tobacco) that require the volatilization of moisture or solvents from the substances. These procedures often use microwave energy to heat a sample to remove various volatiles, such as solvents or moisture. Thereafter, moisture, solids, or other residuals and losses can be determined. To achieve these weight measurements rapidly and accurately, the sample is not removed from the balance, but rather weighed in place after each succeeding step. Preferably, the weight of the substance is sensed or measured repeatedly during the microwave heating while volatile species are still being driven from the heated sample. Such procedures not only require sensitive analytical balances, but the capability to measure weight while the sample is hot.

Those having ordinary skill in the art will understand that, when placed in cool environments, hot substances generate convection currents that cause air to flow around the heated substances. These air currents can interfere with the ability of analytical balances to obtain accurate weight measurements. For example, analytical balances should be accurate within plus or minus 0.10 milligram to facilitate completion of the desired analytical procedures. At these kinds of error margins, convection currents can substantially affect the measured results and impair procedural reproducibility.

U.S. Pat. No. 4,291,775 (hereinafter the Collins '775 patent), which is commonly assigned with this application, addresses the problem of disruptive convection currents and is incorporated entirely herein by reference. More specifically, the Collins '775 patent describes a method and apparatus for improving the weighing accuracy of sensitive automatic balances when weighing heated substances. The Collins '775 patent accomplishes this by introducing an air barrier shield to cover the balance plate without contacting or touching the automatic balance. This tends to reduce the convection currents that can interfere with the sensitive balance and hinder the achievement of accurate sample weight measurements. In other words, eliminating convection air currents reduces movement of the balance and, thereby, fluctuations in the measurement of sample weight being sensed. The Collins '775 patent teaches that the air barrier is permeable to microwave radiation and capable of absorbing moisture and other volatilized substances while being substantially impermeable to air currents. In particular, the Collins '775 patent teaches that glass fiber matting or padding is particularly useful for forming the air barrier enclosure. U.S. Pat. No. 4,291,775 is hereby entirely incorporated by reference.

Although the method and apparatus disclosed by the Collins '775 patent is useful and effective, its employment of a portable air barrier can be somewhat awkward. In particular, an operator using the apparatus must place sample material on a balance plate, which is positioned within the microwave oven cavity. Then, the operator must position the barrier over the balance plate and the sample material such that the barrier does not come in contact with the balance plate and the sample material. Because the air barrier is not affixed to the microwave oven, however, the operator must position the barrier such that it rests upon the floor of the microwave oven. Consequently, heating of the sample material is delayed while the operator manipulates the portable barrier.

Moreover, even though the barrier disclosed by the Collins '775 patent is permeable to microwave radiation and absorbent of moisture and solid vapors, its confining structure, whether a box, cone, or dome, tends to capture and condense more volatiles than can be transported through the barrier for re-volatilization. This increases the concentration of condensates under the portable barrier, thereby slowing the vaporization rate of the sample material and, thus, the length of the test procedure.

OBJECT AND SUMMARY OF THE INVENTION

Therefore, it is an object of this invention to improve upon the apparatus design of the Collins '775 patent by including an air shield that is removably secured to the inside of the heating cavity such that the air shield does not contact the analytical balance when the air shield is fastened to the heating cavity. By securing the air shield to the interior of the microwave cavity, a laboratory technician need not manipulate a movable barrier that must rest on the cavity floor, yet be placed so that the barrier substantially surrounds both the balance plate (e.g., a balance stem) and the sample to be heated.

Accordingly, in one aspect, the invention is an apparatus that facilitates accurate sample weight measurements during sample heating by positioning within a heating cavity a microwave permeable air shield that substantially reduces the convection currents that disrupt accurate sample weight measurements.

In another aspect, the invention is an apparatus that promotes the removal of volatile species from a sample by using an air shield that is an integral part of the heating cavity to condense, transport, and re-volatilize the volatile species freed from the sample.

In another aspect, the invention is an apparatus that promotes microwave heating of a sample by focusing microwave energy upon a sample via the advantageous positioning of a microwave permeable air shield.

In yet another aspect, the invention is a method of exhausting from the cavity volatiles freed from a sample during heating while arresting the development of disruptive convection currents.

The foregoing, as well as other objectives and advantages of the invention and the manner in which the same are accomplished, is further specified within the following detailed description and its accompanying drawings.

BRIEF DESCRIPTION OF THE DRAWINGS

FIG. 3 depicts an expected commercial embodiment of the apparatus.

DETAILED DESCRIPTION OF THE INVENTION

Figure 1:
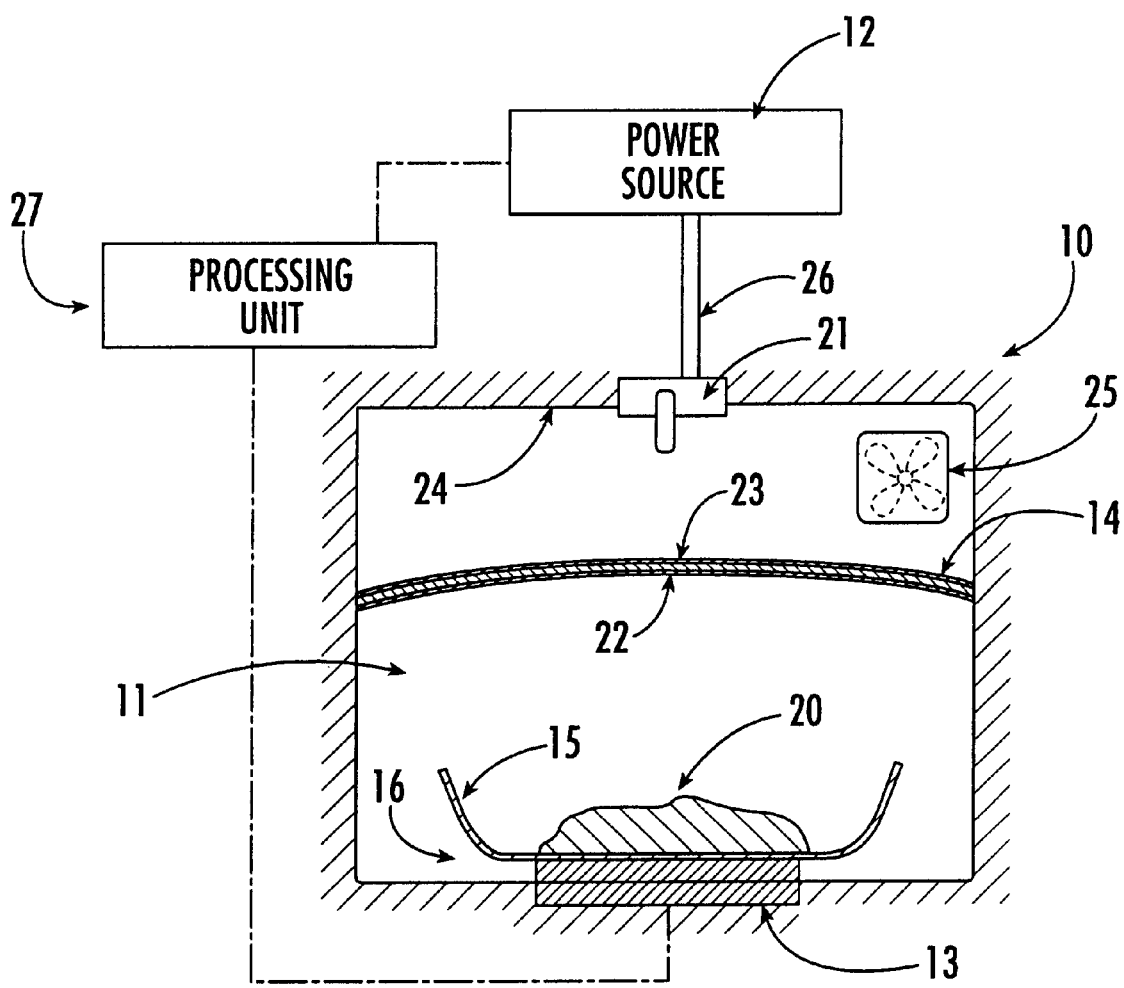
FIG. 1 depicts a schematic sectional view of the apparatus.

The invention is an apparatus that facilitates accurate sample weight measurements during sample heating within a heating cavity by substantially reducing the convection currents that disrupt accurate sample weight measurement. The apparatus includes a heating cavity in which a sample can be placed, a source for introducing microwaves into the heating cavity, and an analytical balance for measuring the weight of the sample while the sample is in the cavity. In this regard, the analytical balance further includes a balance plate that is positioned inside the heating cavity. It is the balance plate that supports the sample. As used herein, the term balance plate is used in a descriptive sense only and should be understood to include an analytical balance stem.

In addition, the apparatus includes an air shield that is secured to the inside of the heating cavity so that the air shield will not contact the analytical balance. This air shield is removable and replaceable. The air shield is positioned in the heating cavity to reduce the convection current rising from the sample as the sample is heated. To function effectively, the air shield must be made of material that is permeable to microwave radiation and yet absorbent of volatiles. In this regard, the term "microwave permeable" means capable of absorbing only small amounts of microwave radiation.

Heated substances generate convection currents (i.e., air streams rising from a heated material) that interfere with the accuracy of analytical balances. The present invention minimizes convection currents by positioning an air shield over a sample that is placed upon an analytical balance. The air shield arrests the convection currents by condensing the volatiles emitted from the heated sample on the surface of the air shield closest to the heated sample (i.e., the first planar surface of the air shield). The air shield, which is made at least in part of a material that is absorbent of condensates (i.e., the condensed volatiles), wicks condensates through moisture-absorbent material to the surface of the air shield opposite the heated sample. After the condensates are transported through the air shield, the condensates absorb microwave radiation and re-volatilize. At this point, the volatiles can be removed from the heating cavity.

As will be understood by those of ordinary skill in this art, polar substances are capable of being heated and volatilized by microwave radiation. Once vaporized, however, polar substances are not as affected by the radiation in the preferred frequency range of between about 900 and 6000 megahertz, particularly the most preferred frequency of about 2450 megahertz, the frequency emitted by conventional magnetrons. In particular, the condensed moisture is wicked from the air shield surface closest to the heated sample (i.e., the first planar surface of the air shield) through to the air shield surface opposite the heated sample (i.e., the second planar surface of the air shield.). At the surface of the air shield opposite the heated sample, the polar condensates are again readily capable of absorbing microwave radiation. Consequently, the condensates that have been transported through the absorbent barrier material are re-volatilized from the second planar surface of the air shield. This takes place without creating air currents that would otherwise affect the weighing of substances on the balance.

The air shield of the present invention is an improvement over the prior art because the air shield is removably fastened to the inside of the heating cavity. As a result, a technician or operator need not manipulate a portable air barrier after placing a sample on the balance plate. Rather, the technician may begin the microwave heating immediately upon placing the sample on the analytical balance plate and securing the heating cavity. Consequently, the present apparatus eliminates testing delays caused by having to position a cumbersome portable air barrier within the confined space that is defined by the heating cavity.

In addition, because the air shield of the present invention is an integral part of the heating cavity, the air shield need not rest on the cavity floor. One weakness with the prior art is that a portable air barrier necessarily surrounds a sample such that condensates accumulate within the air barrier structure. As will be understood by those having ordinary skill in the art, this substantially enclosed environment underneath the barrier that is rich in volatiles and condensates slows the mass transport of volatiles through the air barrier. This slowed removal of volatilized species leads to longer drying times and, hence, more time-consuming test procedures. In contrast, the air shield of the present invention arrests convection currents without substantially enclosing the sample in a barrier structure.

The present invention can be described with reference to FIG. 1, a schematic sectional view of the apparatus in its broadest aspects. Apparatus 10 includes heating cavity 11, source 12, analytical balance 13, and air shield 14. Analytical balance 13 is positioned within apparatus 10 such that at least balance plate 15 of analytical balance 13 is positioned inside heating cavity 11, preferably above cavity floor 16. Preferably, analytical balance 13 is positioned below cavity floor 16. Balance plate 15, which is designed to support material sample 20, is preferably a balance stem.

Radiant heat, preferably microwave radiation, is directed into cavity 11 from source 12 through radiation inlet 21. As will be understood by those having ordinary skill in the art, appropriate reflectors, mixers, radiation absorbers, and the like are preferably provided so as to disperse microwave radiation toward sample material 20 as it is situated on balance plate 15. This technology is well understood and so will not be herein discussed.

Air shield 14 further comprises first planar surface 22 closest to the heated sample and second planar surface 23 opposite the heated sample. As discussed previously, air shield 14 is permeable to microwave radiation and yet absorbent of moisture and solvent vapors. In particular, air shield 14 must be capable of absorbing condensates from convection currents rising from sample material 20, wicking the condensates from first planar surface 22 of the air shield 14 through air shield 14 to second planar surface 23 of the air shield 14, and thereafter permitting the evaporation of the condensates to occur at second planar surface 23. Consequently, air shield 14 restricts the flow of low-pressure air, such as that generated by convection currents.

Suitable microwave-permeable materials include natural and synthetic fibers (e.g., nylon, polyesters, cellulose acetates, acrylics, cotton, wool, flax, glass fibers, Teflon fibers, and polypropylene fibers). These kinds of materials tend not to decompose when subjected to microwave radiation. Moreover, they absorb moisture and solvents. The fibers can be either woven or nonwoven. Woven glass fibrous materials are readily available and function effectively, as do nonwoven padding and matting. In addition, sheet material formed from these kinds of fibers are appropriate as well (e.g., paper). The preferred fibrous material is glass fiber.

In one preferred embodiment, air shield 14 is fastened to inner ceiling 24 of heating cavity 11, directly above balance plate 15 upon which sample 20 is placed. In another preferred embodiment, air shield 14 is capable of focusing microwave energy onto sample 20 that is placed on balance plate 15.

In yet another preferred embodiment, apparatus 10 also includes exhaust means 25 for removing from heating cavity 11 the volatiles freed from sample 20 as it absorbs microwave energy. This is preferably accomplished using an exhaust fan that directs a flow of ambient air across second planar surface 24 of air shield 14 to thereby re-volatilize condensates that have migrated through air shield 14. The flow of air also cools air shield 14 relative to the convection current and heated sample 20, thereby increasing the rate of condensation of the volatilized species rising from heated sample 20 at first planar surface 22. Accordingly, when exhaust means 25 are incorporated into the apparatus, air shield 14 not only serves to substantially reduce the convection currents within cavity 11, but also prevents exhaust means 25 from blowing air into cavity 11 in such a way as to disrupt the performance of analytical balance 13.

As will be understood by those having ordinary skill in the art, source 12 may be selected from numerous devices for generating microwaves, including magnetrons, klystrons, and various solid-state devices. Magnetrons are the preferred power source. Source 12 can also embrace other heating means, such as radiant or ultraviolet wave heating. Similarly, apparatus 10 can include waveguide 26 for directing microwaves from source 12 to heating cavity 11. In addition, apparatus 10 can further include processing unit 27 in communication with source 12 and analytical balance 13 to facilitate calculations, such as sample moisture content.

Figure 2:
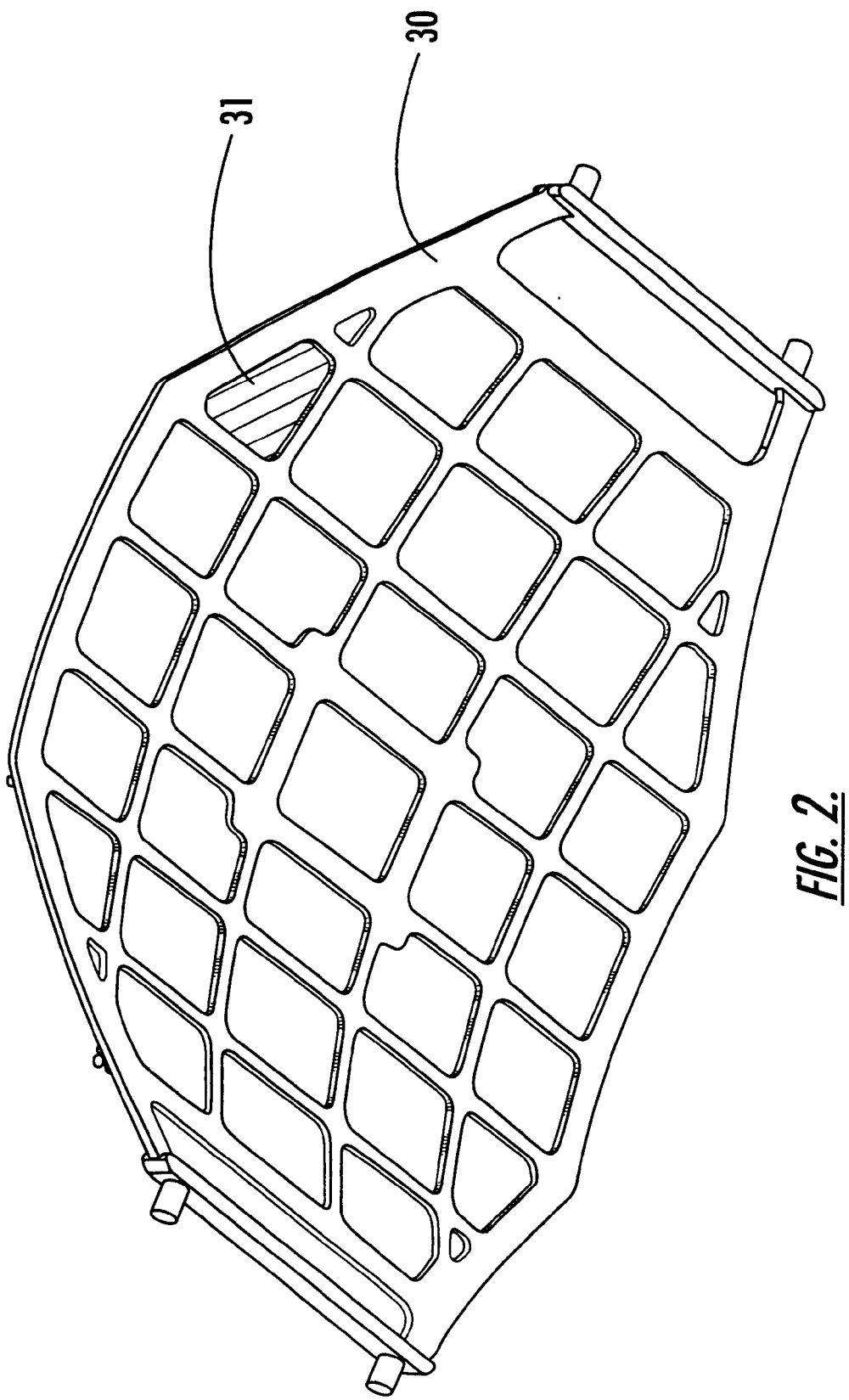
FIG. 2 depicts the preferred embodiment of the air shield.

FIG. 2 depicts the preferred embodiment of air shield 14, wherein air shield 14 has a grid-like framework 30. Framework 30 is made of a material that is permeable to microwave radiation, but that is effectively impermeable to moisture. Preferably, framework 30 is formed from plastic, ceramic, or glass. Although the grids formed by framework 30 need not be of any particular shape or size, grids having a diameter of between about 0.25 and 3 inches are preferred. It will be understood by those of ordinary skill in the art, however, that the size of the grid openings is largely dependent upon the capacity of heating cavity 11. In preferred embodiments, air shield 14 also possesses an arched, planar structure. This tends to focus microwave energy toward balance plate 15 and, more specifically, onto sample 20.

As discussed previously, to function effectively air shield 14 must be capable of absorbing species volatilized from sample 20 as it dries. Accordingly, the grid openings are fitted with pads 31 that are permeable to microwave radiation and absorbent of volatile species that condense on first planar surface 22 of air shield 14. Microwave-permeable, moisture-absorbent pads 31 are preferably made of glass fibers. To ensure sufficient mass transport of the condensed volatiles, microwave-permeable, moisture-absorbent pads 31 are preferably less than 1 mm thick.

FIG. 3 depicts an expected commercial embodiment of apparatus 10. Here, heating cavity 11 is formed in part by hinged cover 40 that is capable of closing over balance plate 15, shown here as a balance stem. It will be understood from FIG. 3 that as hinged cover 40 is closed, microwave cavity 11 is securely formed. It should be noted, too, that this commercial embodiment includes radiation trench 41 that is formed into cavity floor 16, the planar working surface of the apparatus. Trench 41 functions as a microwave choke to prevent microwave energy from escaping from apparatus 10 as microwave energy is introduced into cavity 11. In another commercial embodiment, the microwave cavity may include a heatable cavity floor that is designed to control the ambient air temperature within the microwave cavity and thereby further reduce condensation within the microwave cavity.

In another aspect, the invention is a method for accurately measuring sample weight during sample heating within a cavity by reducing the adverse influence of convection currents. The method initially includes the steps of placing a sample in a cavity capable of restricting the transmission of microwaves, measuring the weight of the sample using an analytical balance, and introducing microwave energy into the cavity to heat the sample. The method preferably includes one or more of the steps of measuring an initial weight of the sample prior to introducing microwave energy into the cavity, continuously measuring the weight of the sample as the microwave power is being introduced into the cavity, or ceasing the introduction of microwave power when the measured weight of the sample over time indicates that the sample is dry.

As will be understood by those having ordinary skill in this art, when the sample is heated, volatile species are freed from the sample. These volatiles rise from the sample by way of convection current until the convection current is intercepted by the air shield. More specifically, the volatiles are condensed at a first planar surface of the air shield, yielding condensates. The condensates are thereupon transported (i.e., wicked) through the air shield's condensate-absorbent material to a second planar surface of the air shield. A continuous flow of air is directed across the second planar surface of the air shield to evaporate the condensates from the second planar surface of the air shield and thereafter to exhaust the re-volatilized condensates from the heating cavity. This continuous flow of air has the added effect of cooling the air shield, which further promotes condensation of volatiles at the first planar surface of the air shield.

As shown in FIG. 3, when the air shield is incorporated into the inner ceiling of the hinged apparatus cover, the method further includes the step of closing the hinged cover of the cavity. In this embodiment, closing the hinged cover positions the air shield directly over the balance plate and the sample.

Finally, the method can further include the step of positioning the air shield in the cavity to focus microwave energy onto the sample placed in the cavity. In a preferred apparatus, the air shield is incorporated into the cavity structure such that simply securing the cavity (i.e., closing the hinged top to prevent the escape of microwave radiation from the apparatus) before the application of microwave energy will accomplish this.

The objectives described herein are further enhanced by incorporating the elements disclosed by the co-pending and commonly assigned applications Ser. No. 09/398,129 (Microwave Volatiles Analyzer with High Efficiency Cavity) and Ser. No. 09/397,825 (Method for Correcting Weight Measurement Errors during Microwave Heating), which are hereby entirely incorporated by reference.

In the drawings and the specification, typical embodiments of the invention have been disclosed. Specific terms have been used only in a generic and descriptive sense, and not for purposes of limitation. The scope of the invention is set forth in the following claims.

That which is claimed is:

1. An apparatus that facilitates accurate sample weight measurements during sample heating within a heating cavity by substantially reducing the convection currents that disrupt accurate sample weight measurement, comprising:

a heating cavity in which a sample can be placed;

a source for introducing microwaves into said heating cavity;

an analytical balance for measuring the weight of the sample while the sample is in said heating cavity, said analytical balance having a balance plate, wherein said balance plate is positioned inside said heating cavity and said balance plate is capable of supporting the sample; and an air shield that is removably secured to the inside of said heating cavity such that said air shield does not contact said analytical balance when said air shield is fastened to said heating cavity, wherein said air shield is positioned in said heating cavity to reduce the convection current rising from the sample as the sample is heated and wherein said air shield comprises a material that is permeable to microwave radiation and absorbent of species volatilized from the sample;

wherein said heating cavity further comprises a hinged cover and said air shield is fastened to an inner ceiling of said hinged cover such that when said hinged cover is closed said air shield is positioned over said balance plate of said analytical balance.

2. A method for accurately measuring sample weight during sample heating within a cavity by reducing the adverse influence of convection currents, comprising:

placing a sample in a microwave cavity;

measuring a weight of the sample using an analytical balance;

introducing microwave energy into the cavity to heat the sample, thereby removing volatiles from the sample;

condensing the volatiles to yield condensates at a first planar surface of an air shield that is permeable to microwave radiation;

transporting the condensates through the air shield to a second planar surface of the air shield; and providing a continuous flow of air across the second planar surface of the air shield, thereby promoting evaporation of the condensates from the second planar surface of the air shield.

3. A method according to claim 2, wherein the step of providing a continuous flow of air across the second planar surface of the air shield cools the air shield, thereby promoting condensation of volatiles at the first planar surface of the air shield.

4. A method according to claim 2, further comprising exhausting from the cavity the condensates that evaporate from the second planar surface of the air shield.

5. A method according to claim 2, further comprising the step of closing a hinged cover of the cavity, thereby positioning the air shield over the sample, after the step of placing a sample in a cavity.

6. A method according to claim 2, further comprising the step of positioning the air shield in the cavity to focus microwave energy onto the sample placed in the cavity.

7. A method according to claim 2, further comprising the step of measuring an initial weight of the sample prior to introducing microwave energy into the cavity.

8. A method according to claim 2, wherein the step of measuring a weight of the sample comprises continuously measuring the weight of the sample as the microwave power is being introduced into the cavity.

9. A method according to claim 2, further comprising ceasing the introduction of microwave power when the measured weight of the sample over time indicates that the sample is dry.

10. An apparatus according to claim 1, wherein said air shield further comprises a grid-like structure made of a material that is permeable to microwave radiation and yet non-absorbent of species volatilized from the sample.

11. An apparatus according to claim 10, wherein said grid-like structure holds pads that are permeable to microwave radiation and absorbent of species volatilized from the sample.

12. An apparatus according to claim 1, wherein said air shield is capable of focusing microwave energy onto the sample placed on said balance plate of said analytical balance when said hinged cover is closed.

13. An apparatus according to claim 1, further comprising exhaust means for removing volatiles from said heating cavity as the sample is being heated therein.

14. An apparatus according to claim 13, wherein said air shield is positioned in said heating cavity to reduce the convection current rising from the sample and to intercept a flow of air that is produced by said exhaust means, such that said air shield is cooler than both the sample being heated and the convection current rising from the sample as the sample is heated.

15. An apparatus according to claim 14, wherein said air shield is capable of adsorbing condensates from the convection current rising from the sample, transporting the condensates through the air shield, and evaporating the condensates into the flow of air that is produced by said exhaust means.

16. An apparatus according to claim 1, further comprising a processing unit in communication with said source and said analytical balance for calculating sample moisture content.

17. An apparatus according to claim 1, wherein said source is selected from the group consisting of magnetrons, klystrons, and solid-state devices for generating microwaves.

18. An apparatus according to claim 1, further comprising a waveguide for directing microwaves from said source to said heating cavity.

19. An apparatus that facilitates accurate sample weight measurements during sample heating within a heating cavity by substantially reducing the convection currents that disrupt accurate sample weight measurement, comprising:

a heating cavity in which a sample can be placed, said heating cavity comprising a hinged cover having an inner ceiling;

a source for introducing microwaves into said heating cavity;

an analytical balance for measuring the weight of the sample while the sample is in said heating cavity, said analytical balance having a balance plate, wherein said balance plate is positioned inside said heating cavity and said balance plate is capable of supporting the sample;

exhaust means for removing volatiles from said heating cavity as the sample is being heated therein; and an air shield that is fastened to said inner ceiling of said hinged cover such that when said hinged cover is closed said air shield is non-contiguously positioned over said balance plate of said analytical balance to focus microwave energy onto the sample placed on said balance plate, to reduce the convection current rising from the sample as the sample is heated, and to intercept a flow of air that is produced by said exhaust means, such that said air shield is cooler than both the sample being heated and the convection current rising from the sample as the sample is heated;

wherein said air shield comprises a grid-like structure made of a material that is permeable to microwave radiation and yet non-absorbent of species volatilized from the sample, and pads that are permeable to microwave radiation and absorbent of species volatilized from the sample, said pads being positioned within said grid-like structure;

wherein said air shield is capable of adsorbing condensates from the convection current rising from the sample, transporting the condensates through the air shield, and evaporating the condensates into the flow of air that is produced by said exhaust means.

* * * * *

UNITED STATES PATENT AND TRADEMARK OFFICE
CERTIFICATE OF CORRECTION

PATENT NO.     : 6,302,577 B1
DATED          : October 16, 2001
INVENTOR(S)    : Jennings et al.

It is certified that error appears in the above-identified patent and that said Letters Patent is hereby corrected as shown below:

Column 1,
Line 7, "09/397,825" should read -- 09/398,130, now U.S. Patent No. 6,268,570 --.

Column 6,
Line 60, "09/397,825" should read -- 09/398,130, now U.S. Patent No. 6,268,570 --.

Signed and Sealed this

Twenty-second Day of October, 2002

Attest:

Attesting Officer

JAMES E. ROGAN
Director of the United States Patent and Trademark Office